United States Patent
Bence et al.

(10) Patent No.: US 10,532,967 B2
(45) Date of Patent: Jan. 14, 2020

(54) PROCESS FOR THE PRODUCTION OF PROPYLENE GLYCOL FROM LACTATE ESTER

(71) Applicant: JOHNSON MATTHEY DAVY TECHNOLOGIES LIMITED, London (GB)

(72) Inventors: Roger Bence, London (GB); Robert Gallen, London (GB); Robert Wild, Stockton-On-Tees (GB)

(73) Assignee: Johnson Matthey Davy Technologies Limited, London (GB)

( * ) Notice: Subject to any disclaimer, the term of this patent is extended or adjusted under 35 U.S.C. 154(b) by 0 days.

(21) Appl. No.: 16/340,838

(22) PCT Filed: Oct. 17, 2017

(86) PCT No.: PCT/GB2017/053145
§ 371 (c)(1),
(2) Date: Apr. 10, 2019

(87) PCT Pub. No.: WO2018/073581
PCT Pub. Date: Apr. 26, 2018

(65) Prior Publication Data
US 2019/0263739 A1    Aug. 29, 2019

(30) Foreign Application Priority Data
Oct. 19, 2016  (GB) .................................. 1617698.4

(51) Int. Cl.
*C07C 29/149*  (2006.01)
*C07C 31/20*  (2006.01)

(52) U.S. Cl.
CPC .......... *C07C 29/149* (2013.01); *C07C 31/205* (2013.01)

(58) Field of Classification Search
CPC ........................... C07C 29/149; C07C 31/205
USPC ......................................................... 568/858
See application file for complete search history.

(56) References Cited

U.S. PATENT DOCUMENTS 6,441,241 B1   8/2002  Cortright et al.

FOREIGN PATENT DOCUMENTS

| GB | 2150560 A | 5/1987 | | |
|---|---|---|---|---|
| WO | WO 82/03854 A1 | 11/1982 | | |
| WO | WO 2009/103682 A1 | 8/2009 | | |
| WO | WO-2009103682 A1 * | 8/2009 | ............. | B01J 23/72 |
| WO | WO 2011/036189 A2 | 3/2011 | | |
| WO | WO-2011036189 A2 * | 3/2011 | ............. | B01J 21/16 |
| WO | WO 2016/081187 A1 | 5/2016 | | |

OTHER PUBLICATIONS

Huang et al., Vapor-Phase Hydrogenolysis of Biomass-Derived Lactate to 1,2-propanediol Over Supported Metal Catalysts, Applied Catalysis A: General, 349 (2008) pp. 204-211.
GB1617698.4 Search Report Under Section 17(5) dated Aug. 31, 2017.
GFB1717043.2 Combined Search and Examination Report Under Sections 17 and 18(3) dated Dec. 6, 2018.
WO2018/073581 International Search Report dated Jan. 3, 2018.
WO2018/073581 Written Opinion dated Jan. 3, 2018.

* cited by examiner

*Primary Examiner* — Deborah D Carr
(74) *Attorney, Agent, or Firm* — BakerHostetler

(57) ABSTRACT

A process for the production of propylene glycol from a lactate ester is disclosed. The process comprises supplying a feed comprising a $C_{3-6}$ alkyl lactate ester. The feed is contacted with a stream of hydrogen containing gas and subjected to hydrogenation in the vapour phase in the presence of a catalyst at a temperature of from about 130° C. to about 185° C., a pressure of from about 20 bar to about 60 bar, and a weight hourly space velocity greater than about 0.3 $h^{-1}$. The catalyst is a reduced copper catalyst selected from copper alumina, optionally comprising manganese, copper chromite, copper zinc oxide and Raney copper.

12 Claims, No Drawings

PROCESS FOR THE PRODUCTION OF PROPYLENE GLYCOL FROM LACTATE ESTER

CROSS-REFERENCE TO RELATED APPLICATIONS

This application is the National Stage of International Patent Application No. PCT/GB2017/053145, filed Oct. 17, 2017, which claims priority to Great Britain Patent Application No. 1617698.4, filed Oct. 19, 2016, the entire disclosures of both of which are incorporated herein by reference for any and all purposes.

The present invention is a process for the hydrogenation of alkyl lactate esters in the vapour-phase. More particularly, the present invention relates to a hydrogenation reaction having improved selectivity for propylene glycol, which is also known as 1,2-propanediol, from butyl lactate and improved conversion of alkyl lactate esters.

Propylene glycol is used in a wide variety of applications, such as monomers in polymer resins, de-icing fluids and food additives. Traditional production routes involve complex conversions of oil-derived feedstocks via propylene and propylene oxide. However, due to the high demand for the production of propylene glycol, it is desirable to diversify the current feedstock. There has, therefore, been a focus on ways in which biological routes can be utilised to obtain propylene glycol, and in particular ways in which propylene glycol can be obtained from waste product streams and renewable sources, such as plants.

It is known that plants produce glucose from atmospheric carbon dioxide and sunlight by photosynthesis. Glucose may also be obtained from a number of natural sources, such as corn starch which is a natural product obtained from corn. Fermentation of glucose is known to produce lactic acid, also known as α-hydroxypropanoic acid or 2-hydroxypropanoic acid, and lactic acid can be used as an alternative feedstock in the production of propylene glycol.

If fermentation and separation technologies could be improved, the price of lactic acid derived from natural resources would fall. The prospect of a reduction in the price of lactic acid has ignited interest in developing cost effective ways of converting the carboxylic acid group of lactic acid to a hydroxyl group in order to produce propylene glycol. Despite the interest in such processes, they suffer from drawbacks because, for example, the catalytic hydrogenation of carboxylic acids is known to be difficult.

In the past, the hydrogenation of carboxylic acids had generally been achieved using a two-step process, in which the carboxylic acid is first converted to an ester or an anhydride, and the ester or anhydride is then reduced further in a second reduction step.

An example of the formation of propylene glycol from lactic acid and lactic acid esters by hydrogenation in the liquid phase is described in U.S. Pat. Nos. 6,403,844 and 9,132,418. However, liquid phase processes suffer from various drawbacks. For example, it is necessary to use high pressures, such as in the region of 100 bar, in order for the reaction to proceed. In addition, increased residence times are required in order for the reaction to proceed. The use of high pressures increases the overall cost of the process because of the specialist equipment that needs to be used and increased residence times result in a slow process, which is commercially unfavourable.

In an attempt to overcome the drawbacks associated with liquid phase processes, there has been a focus on the hydrogenation of organic esters to produce alcohols and glycols in the vapour phase. The vapour phase processes primarily focus on the reduction of lactic acid and esters of lactic acid and they aim to reduce the overall pressure of the process. Examples of these processes can be seen in WO 82/03854 and WO 2011/036189. However, as explained in U.S. Pat. No. 6,441,241, lactic acid can undergo hydrogenation despite its low thermal stability.

Attempts to improve vapour-phase processes have focussed on adjusting variables in the hydrogenation reaction. For example, it has been suggested in Huang et al., Applied Catalysis A: General 349, 2008, 204-211, that cobalt catalysts are more active in terms of both conversion and selectivity under mild conditions when compared with traditional copper catalysts.

Whilst performing reactions in the vapour-phase offers an improvement over liquid-phase processes, but there are still drawbacks. As described in Huang et al, a reduction in pressure reduces the selectivity for the final product. This may not be an issue when the main by-product is, for example, hydroxypropanone, as it can be polished out at high selectivity. However, the formation of propanols, i.e. n-propanol and iso-propanol as by-products is disadvantageous as they cannot be readily converted to the desired product, which results in a loss of feedstock.

Similarly, an increase in temperature reduces the selectivity to the final product, whereas a reduction in temperature reduces the conversion of the feedstock. Additionally, and as described in WO 2011/036189, an increase in weight hourly space velocity (WHSV) impacts on both conversion of feedstock and selectivity to propylene glycol. An increase in WHSV typically decreases both conversion and selectivity.

There therefore remains a need for processes for producing propylene glycol which address one or more of the problems of the problems of the prior art. Thus it is desirable to provide a process which has one or more of an improved throughput, a maximised conversion of the alkyl lactate ester feedstock and minimised production of by-products. Surprisingly, it has been found that this can be achieved by using specific process conditions, namely a pressure of from about 20 bar to about 60 bar and a temperature of from about 140° C. to about 180° C., and a catalyst selected from copper alumina, optionally comprising manganese, copper chromite, copper zinc oxide and Raney copper.

Thus, according to a first aspect of the invention, there is provided a process for the production of propylene glycol from a lactate ester, the process comprising supplying a feed comprising a O3-6 alkyl lactate ester, wherein the feed is contacted with a stream of hydrogen-containing gas and subjected to hydrogenation in the vapour-phase in the presence of a catalyst at a temperature of from about 130° C. to about 185° C., a pressure of from about 20 bar to about 60 bar, and a weight hourly space velocity greater than about 0.3 $h^{-1}$, and wherein the catalyst is a reduced copper catalyst.

The use of the above process conditions and catalyst have been found to be particularly advantageous in terms of improving selectivity for propylene glycol and improving conversion of the alkyl lactate ester relative to existing processes and existing vapour-phase processes. Additionally, the process conditions set out above typically allow for retention of catalytic activity, which results in a higher throughput when compared with existing processes.

In a further aspect of the invention, the lactate ester may be vaporised into a stream of hydrogen-containing gas in a vaporiser before being passed to a hydrogenation reactor. Any suitable vaporiser may be used, provided it enables vaporisation of the lactate ester. Suitable vaporisers include a falling film evaporator, a thin film vaporiser, a wiped film evaporator, a kettle vaporiser, or the like.

Any suitable reduced copper catalyst may be used. Suitable catalysts include copper alumina, copper chromite, copper zinc oxide and Raney copper. Where the catalyst is copper alumina, it may comprise manganese. In one arrangement, the catalyst may be a copper/alumina/manganese catalyst or a copper chromite catalyst. In some arrangements, more than one catalyst may be present. The catalyst may be provided to the reactor in any suitable form. It may be provided in particulate form. The catalyst may be provided as a fixed bed in the hydrogenation reactor.

The feed comprises a $C_{3-6}$ alkyl lactate ester. Any suitable $C_{3-6}$ alkyl lactate ester may be used. In some arrangements, the feed comprises a $C_{4-5}$ alkyl lactate ester. In some aspects, the feed may comprise one or more $C_{3-6}$ alkyl lactate esters. In one arrangement, the feed may be a butyl lactate ester.

The term "alkyl" includes a straight or branched saturated monovalent hydrocarbon radical, having the number of carbon atoms as indicated. For example, the term "$C_{3-6}$ alkyl" includes $C_3$, $C_4$, $C_5$ and $C_6$ alkyl groups. By way of non-limiting example, suitable alkyl groups include n-propyl, iso-propyl, butyl, iso-butyl, tert-butyl, pentyl and hexyl.

The process of the invention is carried out at a temperature of from about 130° C. to about 185° C. and a pressure of from about 20 bar to about 60 bar. The temperature and pressure selected will depend on the alkyl-lactate ester that is to be hydrogenated. In one arrangement, the temperature may be from about 140° C. to about 180° C., or from about 145° C. to less than 180° C., or from about 150° C. to about 175° C., or from about 155° C. to about 175° C., or from about 160° C. to about 175° C. The pressure may be selected from about 30 bar to about 55 bar, or from about 35 bar to about 50 bar, or from about 40 bar to about 45 bar.

The process of the present invention may be capable of tolerating increased throughput, which can be measured by increasing the weight hourly space velocity (WHSV). The WHSV is a measure of the mass of liquid feed per mass of catalyst per hour. In one arrangement, the WHSV may be greater than about $0.3\ h^{-1}$. The WHSV may also be from about $0.3\ h^{-1}$ to about $2.0\ h^{-1}$, or from about $0.4\ h^{-1}$ to about $1.8\ h^{-1}$, or from about $0.5\ h^{-1}$ to about $1.6\ h^{-1}$, or from about $0.6\ h^{-1}$ to about $1.4\ h^{-1}$, or from about $0.7\ h^{-1}$ to about $1.2\ h^{-1}$.

It will be understood that the molar hydrogen to ester ratio will be such that the reactant stream passing over the catalyst remains in the vapour phase at the process conditions and thus the molar ratio selected will depend on the temperature and pressure selected. For example, where the process is carried out at a temperature of about 185° C. and a pressure of about 20 bar, a hydrogen to ester ratio may be about 18:1, where the process is carried out at a temperature of about 130° C. and a pressure of about 20 bar, a hydrogen to ester ratio may be about 120:1, where the process is carried out at a temperature of about 130° C. and a pressure of about 60 bar, a hydrogen to ester ratio may be about 55:1, and where the process is carried out at a temperature of about 185° C. and a pressure of 60 bar, a hydrogen to ester ratio may be about 365:1.

In general, the molar hydrogen to alkyl lactate ester ratio may be from about 10:1 to about 600:1. In a further arrangement, the molar hydrogen to alkyl lactate ester ratio may be from about 20:1 to about 500:1, or from about 30:1 to about 450:1, from about 50:1 to about 400:1, or from about 100:1 to about 300:1, or about 200:1.

The type of reactor and reactants that are used may impact on the catalyst and reaction conditions that are used. Accordingly, it will be understood that combinations of the catalysts, temperatures, pressures, hydrogen to ester ratios and WHSVs set out above are also envisaged. For example, it will be understood that processes are provided for in which the catalyst is a copper/alumina/manganese catalyst, the temperature is from about 145° C. to about 175° C., the pressure is from about 40 bar to about 50 bar, the hydrogen to ester ratio is from about 450:1 to about 300:1 and the WHSV is from about $0.4\ h^{-1}$ to about $1.8\ h^{-1}$. Similarly, processes are provided for wherein the catalyst is a copper/alumina/manganese catalyst, the temperature is from about 150° C. to about 175° C., the pressure is from about 35 bar to about 55 bar, the hydrogen to ester ratio is from about 100:1 to about 400:1 and the WHSV is from about $0.5\ h^{-1}$ to $1.6\ h^{-1}$.

In one aspect, the process of the present invention results in excellent conversion of alkyl lactate esters to propylene glycol. An improvement in conversion compared with existing process may be obtained. The improvement in conversion over existing processes may be about a 5% improvement, about a 7% improvement, about an 8% improvement, or about a 10% improvement. In general, conversions in excess of from about 95% mol, in excess of from about 96% mol, in excess of from about 97% mol, in excess of from about 98% mol or in excess of from about 99% mol may be obtained.

Although excellent conversion of the alkyl lactate ester is obtained by the process disclosed above, it will be understood that additional improvements in conversion may be obtained by polishing the post-reaction product. Suitable polishing steps are described in U.S. Pat. No. 8,334,416, which is hereby incorporated by reference.

In another aspect, the process of the present invention results in excellent selectivity for propylene glycol by reducing the amount of by-products that are formed. An improvement in selectivity compared with existing processes may be obtained. The improvement in selectivity over existing processes may be about a 5% improvement, about a 7% improvement, about an 8% improvement, or about a 10% improvement. In some aspects, selectivity for propylene glycol may be in excess of from about 97% mol, in excess of from about 98% mol, or in excess of from about 99% mol.

In still another aspect, the process of the present invention results in improved throughput, which may be determined by measuring conversion of the alkyl lactate ester and/or selectivity for propylene glycol as WHSV increases. The excellent conversion and/or selectivity discussed above may be retained as WHSV increases. The excellent conversion of alkyl lactate ester feedstock is said to be retained following an increase in WHSV if the percentage reduction in conversion is no more than about 10%, no more than about 8%, no more than about 6%, no more than about 5%, no more than about 3%. The excellent selectivity for propylene glycol is said to be retained following an increase in WHSV if the percentage reduction in selectivity is no more than about 10%, no more than about 8%, no more than about 6%, no more than about 5%, no more than about 3%.

It will, of course, be understood that the process of the present invention may result in excellent conversion and excellent selectivity. Similarly, it will be understood that excellent selectivity and excellent conversion may be retained as throughput increases (WHSV increases).

The present invention will now be described with reference to the accompanying examples.

EXAMPLES 1 TO 5

Liquid butyl lactate was evaporated into a hot stream of hydrogen at pressure. The gaseous mixture of hydrogen and butyl lactate was then fed into a tubular reactor packed with catalyst. The reactor inlet temperature was maintained at the desired temperature by trace heating and insulation of the feed line. The reactor was maintained as an adiabatic reactor by provision of electric trace heating and insulation. The reactor vapour effluent was condensed in a chiller so that the liquid could be collected for gas chromatography analysis. The details are set out in Table 1.

TABLE 1

| Example | Pressure (barg) | Inlet Catalyst (° C.) | Ester Flow (g/h) | Hydrogen NLPH | $H_2$:Ester Ratio (molar) | Conversion Mol % | Selectivity to propylene glycol (mol %) | STY ($h^{-1}$) |
|---|---|---|---|---|---|---|---|---|
| 1 | 40 | 173 | 31 | 7269 | 1583 | 97.63 | 98.08 | 0.176 |
| 2 | 40 | 170 | 60 | 1083 | 121 | 96.94 | 98.20 | 0.342 |
| 3 | 40 | 156 | 114 | 2435 | 141 | 99.97 | 98.74 | 0.406 |
| 4 | 40 | 156 | 114 | 2426 | 140 | 99.96 | 98.75 | 0.406 |
| 5 | 40 | 156 | 114 | 2435 | 141 | 99.97 | 98.74 | 0.405 |

STY = space time yield, which is the mass of propylene glycol produced per hour per mass of catalyst

The invention claimed is:

1. A process for the production of propylene glycol from a lactate ester comprising
supplying a feed comprising a $C_{3-6}$ alkyl lactate ester, wherein the feed is contacted with a stream of hydrogen-containing gas and subjected to hydrogenation in the vapour-phase in the presence of a catalyst at a temperature of from about 130° C. to about 185° C., a pressure of from about 20 bar to about 60 bar, and a weight hourly space velocity greater than about 0.3 $h^{-1}$, and
wherein the catalyst is a reduced copper catalyst selected from copper alumina, optionally comprising manganese, copper chromite, copper zinc oxide and Raney copper.

2. The process according to claim 1, wherein the lactate ester is vaporised into a stream of hydrogen-containing gas in a vaporiser before being passed to a hydrogenation reactor.

3. The process according to claim 2, wherein the catalyst is a fixed bed catalyst that is present in the hydrogenation reactor.

4. The process according to claim 1, wherein the catalyst is selected from a copper/alumina/manganese catalyst or a copper chromite catalyst.

5. The process according to claim 1, wherein the catalyst is a copper/alumina/manganese catalyst.

6. The process according to claim 1, wherein the feed comprises butyl lactate ester.

7. The process according to claim 1, wherein the hydrogen to alkyl lactate ester molar ratio is from about 10:1 to about 600, or about 20:1 to about 500:1, or about 250:1.

8. The process according to claim 1, wherein the temperature is from: about 140° C. to about 180° C.; or from about 145° C. to less than 180° C.; or from about 150° C. to about 175° C.; or from about 155° C. to about 175° C.

9. The process according to claim 1, wherein the temperature is from about 160° C. to about 175° C.

10. The process according to claim 1, wherein the pressure is from about 30 bar to about 55 bar; or from about 35 bar to about 50 bar.

11. The process according to claim 1, wherein the pressure is from about 40 bar to about 45 bar.

12. The process according to claim 1, wherein the weight hourly space velocity is from about 0.3 $h^{-1}$ to about 2.0 $h^{-1}$; or from about 0.4 $h^{-1}$ to about 1.8 $h^{-1}$; or from about 0.5 $h^{-1}$ to about 1.6 $h^{-1}$; from about 0.6 $h^{-1}$ to about 1.4 $h^{-1}$, or from about 0.7 $h^{-1}$ to about 1.2 $h^{-1}$.

* * * * *